United States Patent
Chin et al.

(10) Patent No.: US 7,402,172 B2
(45) Date of Patent: Jul. 22, 2008

(54) INTRALUMINAL THERAPEUTIC PATCH

(75) Inventors: Yem Chin, Burlington, MA (US); (Lenny) Kinh-Luan D. Dao, Randolph, MA (US); Paul Scopton, Winchester, MA (US); (Samuel) Sheng-Ping Zhong, Shrewsbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 365 days.

(21) Appl. No.: 10/962,689

(22) Filed: Oct. 13, 2004

(65) Prior Publication Data

US 2006/0079957 A1 Apr. 13, 2006

(51) Int. Cl.
*A61F 2/06* (2006.01)

(52) U.S. Cl. ............... 623/1.42; 606/151; 424/423

(58) Field of Classification Search ........ 623/1.11–1.51; 606/151; 424/423
See application file for complete search history.

(56) References Cited

U.S. PATENT DOCUMENTS

| | | | | |
|---|---|---|---|---|
| 4,950,475 | A * | 8/1990 | Vishnupad et al. ....... | 514/772.3 |
| 5,399,352 | A * | 3/1995 | Hanson .................... | 424/423 |
| 5,571,172 | A * | 11/1996 | Chin ........................ | 128/898 |
| 5,749,915 | A | 5/1998 | Slepian | |
| 5,782,789 | A * | 7/1998 | Herweck et al. .......... | 602/52 |
| 5,827,265 | A | 10/1998 | Glinsky et al. | |
| 6,162,456 | A | 12/2000 | Dunbar et al. | |
| 6,375,963 | B1 | 4/2002 | Repka et al. | |
| 6,409,716 | B1 | 6/2002 | Sahatjian et al. | |
| 6,517,571 | B1 | 2/2003 | Brauker et al. | |
| 6,531,641 | B2 | 3/2003 | Ashman | |
| 6,613,084 | B2 * | 9/2003 | Yang ........................ | 623/1.42 |
| 7,083,644 | B1 * | 8/2006 | Moroni .................... | 623/1.51 |
| 2002/0049503 | A1 * | 4/2002 | Milbocker ............... | 623/23.72 |
| 2002/0062147 | A1 | 5/2002 | Yang | |
| 2003/0073979 | A1 | 4/2003 | Naimark et al. | |
| 2003/0138950 | A1 * | 7/2003 | McAllister et al. ........ | 435/366 |
| 2004/0024419 | A1 | 2/2004 | Slepian et al. | |
| 2006/0173471 | A1 * | 8/2006 | Carr et al. ................ | 606/151 |

(Continued)

FOREIGN PATENT DOCUMENTS

WO 01/89594 A2 11/2001

OTHER PUBLICATIONS

"Gelva pressure sensitive adhesives," http://www.solutia.com/pages/corporate/products/product.asp?product=110.

(Continued)

*Primary Examiner*—Suzette J Gherbi
(74) *Attorney, Agent, or Firm*—Kenyon & Kenyon LLP (57) ABSTRACT

The present invention includes systems, methods and apparatus. A system in accord with the present invention may include an intraluminal patch sized to fit within a lumen and an expandable therapeutic delivery device. The patch in this embodiment may have an adhesive region on an exposed surface and a drug reservoir region in communication with the exposed surface. By comparison, a method employing the present invention may include placing an intraluminal patch over an expandable delivery device, advancing the delivery device and the expandable patch to a target site, expanding the delivery device so that the patch adheres to the target site, and contracting and withdrawing the delivery device. In so doing the patch may remain to emit a drug to the target site over a sustained period of time.

16 Claims, 6 Drawing Sheets

U.S. PATENT DOCUMENTS

2007/0135906 A1* 6/2007 Badylak et al. ............ 623/1.44

OTHER PUBLICATIONS

"Pressure Sensitive Adhesives," http://www.velcro.com/industrial/pressure.html.

"Adhesive Guide," http://www.pointil.com/resources/adhesive.htm.

Donald V. Varanese, "The Fundamentals of Selecting Pressure-Sensitive Adhesives," http://www.devicelink.com/mpb/archive/98/01/002c.html.

Donald Satas, ed., "Handbook of Pressure Sensitive Adhesive Technology," 3rd Ed., http://www.polysurfacesbookstore.com/pages/3345.html.

* cited by examiner

FIG. 14 ic delivery. More
INTRALUMINAL THERAPEUTIC PATCH

FIELD OF THE INVENTION

The present invention regards therapeutic delivery. More specifically, the present invention regards the delivery of therapeutic by transporting therapeutic to a target site within the body of a patient and then depositing the therapeutic at the target site, the therapeutic being carried to the target site with a deployable patch.

BACKGROUND

The delivery of therapeutic to a target site or region in the body of a patient is a procedure that is often repeated in contemporary medicine. Contemporary therapeutic delivery techniques can range from hypodermic needle injections performed outside of the body, to the placement of implants deep within the body of a patient. As can be imagined, the former is practically non-invasive while the later procedure is highly invasive.

In some instances, therapeutic may also be delivered through slightly invasive techniques. These include the intraluminal delivery of coated stents to a diseased blood vessel in the body. These stents may be delivered through the positioning and expansion of a balloon catheter within the body. In this example, as well as with other coated implants, the implant itself is generally a rigid structure intended for long-term dwelling within the body.

SUMMARY OF THE INVENTION

The present invention includes systems, methods, and apparatus for delivering therapeutic. A system in accord with the present invention may include an intraluminal patch sized to fit within a lumen and an expandable therapeutic delivery device. The patch in this embodiment may have an adhesive region on an exposed surface and a drug reservoir region in communication with the exposed surface. By comparison, a method employing the present invention may include placing an intraluminal patch over an expandable delivery device, advancing the delivery device and the expandable patch to a target site, expanding the delivery device so that the patch adheres to the target site, and contracting and withdrawing the delivery device. In so doing the patch may remain to emit a therapeutic to the target site over a sustained period of time.

Another method employing the present invention may include delivering and bonding the intraluminal patch to the target site. In so doing, in addition to delivering therapeutic to the target site, moisture may also be absorbed by the patch, away from the target site.

DETAILED DESCRIPTION

Figure 1:
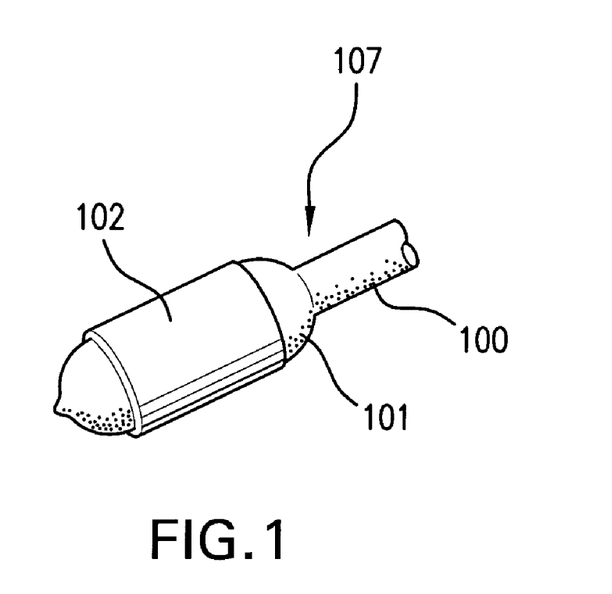
FIG. 1 is a perspective view of an intraluminal patch positioned about an expandable balloon catheter in accord with an embodiment of the present invention.

FIG. 1 is a therapeutic delivery system 107 in accord with an embodiment of the present invention. In the delivery system 107 of FIG. 1, an intraluminal patch 102 is disposed over an expandable balloon 101 of a delivery catheter 100. The intraluminal patch 102 may be positioned in the delivery system 107 such that it may be pressed against a target site when the balloon is positioned near the target site and subsequently expanded. Once pressed onto the target site, the intraluminal patch may remain there to deliver therapeutic, stop unwanted bleeding or perform other desired functions. The intraluminal patch 102 may contain an adhesive to secure the patch 102 to the target site. This adhesive is preferably strong enough to allow the patch 102 to be firmly secured to the target site, slowing or stopping any localized hemorrhaging while also delivering therapeutic to the region over short or prolonged periods of time. The adhesive may be placed on the patch along the patch's periphery as well as on other portions of its surface. The adhesives may be pressure sensitive so that the amount of force placed on the patch will influence the adhesive bond between the patch and the target area. The forces placed on the patch by the expanding balloon may not only act to seat the patch at the target site but they may also act to force residual body fluid out from behind the patch 102 as the patch is seated against and adhered to the target site.

The expandable balloon 101 can be made of various thermoplastic materials, including polyethylene, PET, polyurethane, PVC, or nylons. Alternatively, the balloon 101 may be made from other materials, including latex, silicone or styrene block copolymers. Other catheters or expandable devices may also be used to carry and deliver the intraluminal patch 102. In each case it is preferred that the device be adapted to be able to apply pressure to the patch or to otherwise be able urge it towards the target site so that the patch may become adhesively secured to the target site.

Figure 2:
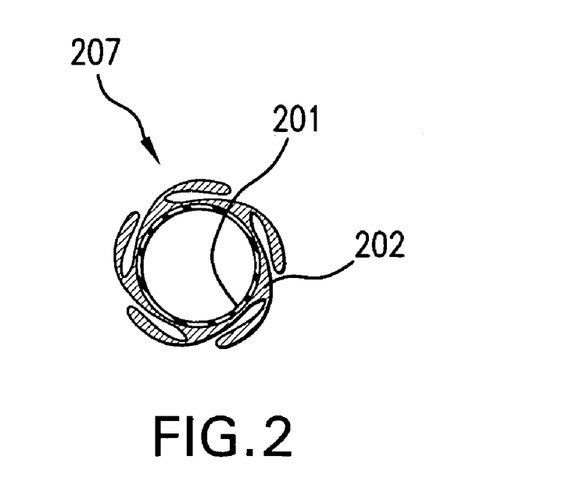
FIG. 2 is a cross-sectional view of another embodiment of the present invention, the embodiment comprising a folded intraluminal patch.

FIG. 2 is a cross-section of a system 207 employing an intraluminal patch 202. In this system 207, the intraluminal patch 202 is positioned around an expandable balloon catheter 201. As can be seen, the intraluminal patch 202 in this embodiment is folded. Accordingly, as the balloon 201 expands the patch 202 may unfold.

It may be preferable to employ a folded patch as shown in this embodiment when the patch is less elastic than the delivery balloon. In so doing, the compressed size of the balloon and patch may have a reduced cross-sectional size when compared to a similar, but unfolded system.

The patch 202 may be deployed from the balloon even if some or all of the folds are not completely unfolded. To accommodate the deployment of a partially unfolded patch 202, adhesive may be placed on all outer surfaces of the patch 202. In so doing, adhesive may be assured to be on the outside of the patch regardless of its final deployed sized and degree of expansion.

Figure 3:
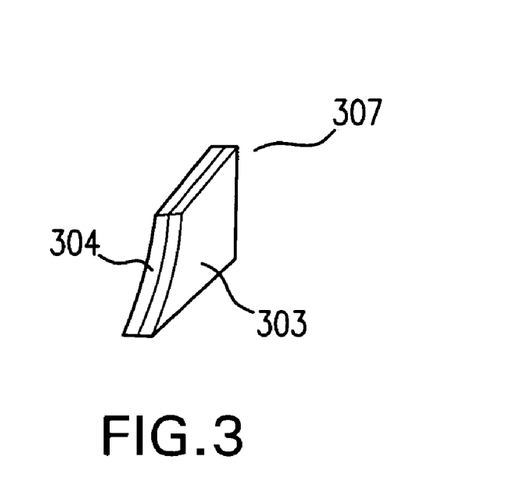
FIG. 3 is a perspective view of another embodiment of the present invention, the embodiment comprising a sheet-shaped intraluminal patch.

FIG. 3 is an embodiment of the present invention where the intraluminal patch has been formed as a sheet rather than as a ring as in FIGS. 1 and 2. In FIG. 3, the intraluminal patch 307 comprises a reservoir region 304 and an adhesive region 303. The patch 307 is shown as a rectangular prism in FIG. 3, however, it may be configured in many other shapes as well. These shapes may be chosen and designed to adapt to specific target sites in the body. The patch 307 in this embodiment, as well as in others, may not only be delivered by securing it to an expandable delivery balloon, but may be delivered by other methods and devices as well. These methods can include direct placement by a medical practitioner and remote placement by medical devices other than balloon catheters.

FIGS. 4-7 show various other configurations and embodiments of the present invention. These configurations, as well as the others discussed herein, may be used independent of each other or in conjunction with one another in the various combinations described herein.

Figure 4:
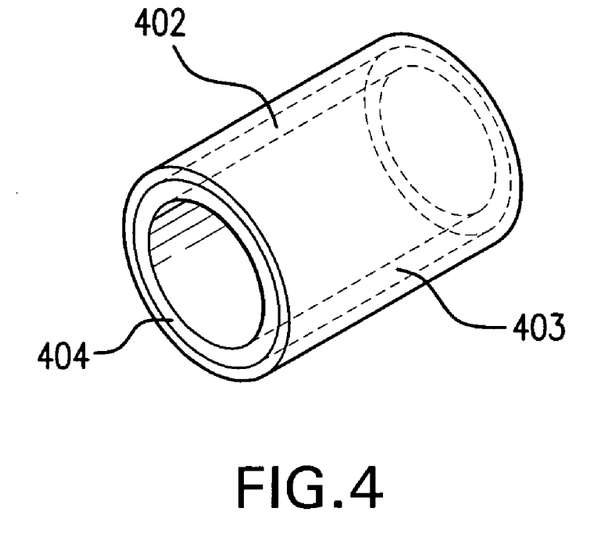
FIG. 4 is a perspective view of another embodiment of the present invention, the embodiment comprising a drug reservoir region within an intraluminal patch.

In FIG. 4 the intraluminal patch 402 is tubular shaped and contains an outer adhesive region 403 and an inner tubular drug reservoir region 404. This embodiment may be useful to deliver therapeutic to an area downstream from where the intraluminal patch is deployed as fluid may course through the patch and carry the therapeutic downstream.

Figure 5:
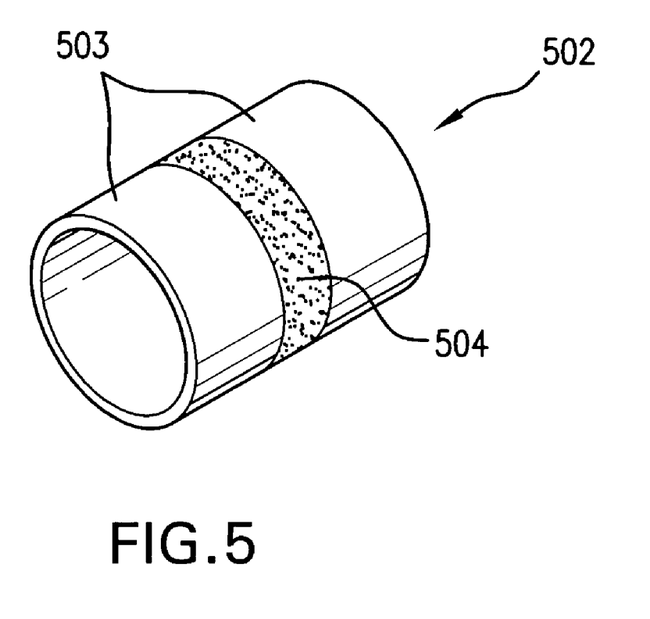
FIG. 5 is a perspective view of another embodiment of the present invention, the embodiment comprising a drug reservoir region on the outer surface of an intraluminal patch.

In FIG. 5 the intraluminal patch 502 is shown with a drug reservoir region 504 exposed along only a portion of the outer adhesive region 503. The size and placement of the exposed portion may coincide with a known injured area at the target site so that the delivery of the therapeutic may be closely managed and tailored. Accordingly, while the adhesive 503 is shown outside of the center of the patch 502, the exact placement of the adhesive region 503 and the drug reservoir region 504 may vary according to the shape and nature of the injury.

Figure 6:
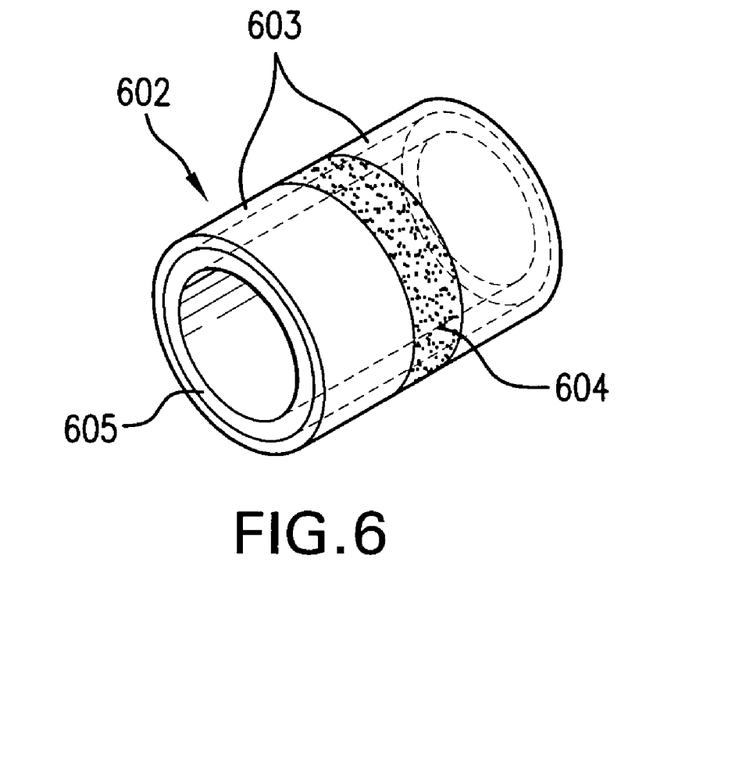
FIG. 6 is a perspective view of an another embodiment of the present invention in which the intraluminal patch employing an inner protective layer.

The intraluminal patch of the present invention may also have a protective layer that protects the patch from damage prior to, during, and after deployment, at the target site. This protective layer may be both inside and outside of the patch. One such example is shown in FIG. 6, which shows a protective layer 605 attached to an inner surface of a patch 602. This protective layer 605 can be used to shield a surface of the patch 602 from moisture or other damaging effects. Wax or a similar non-absorbent barrier substance may used as the protective layer 605. The protective layer 605 may also comprise a dissolvable powder, film, or other non-toxic biodegradable substance that may substantially dissipate by the time the patch is advanced to a target site. Moreover, a protective layer 605 that is permeable only to the therapeutic being emitted may also be used when the protective layer covers the drug reservoir region 604. Still further, the protective layer 605 may also comprise a slidable protective sheath. This sheath may be slid to expose the therapeutic carried by the patch 602 at the appropriate point and time during delivery.

Figure 7:
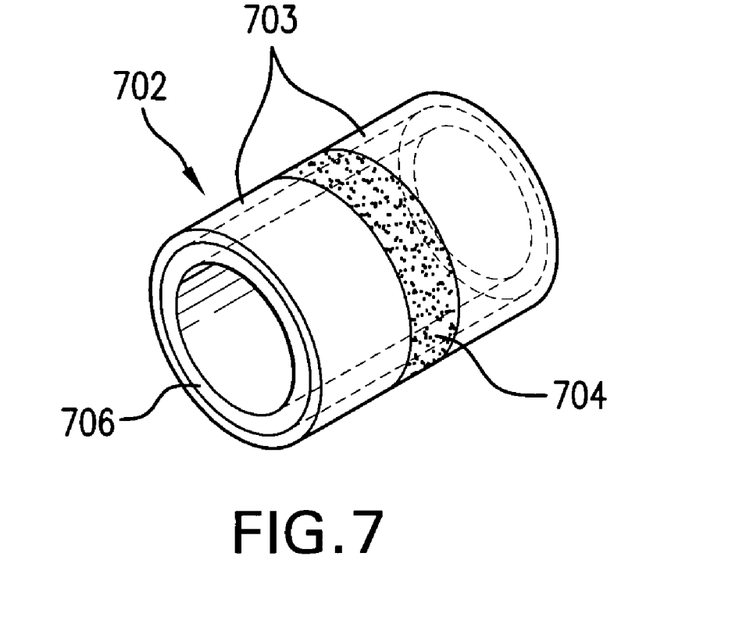
FIG. 7 is a perspective view of another embodiment of the present invention in which the intraluminal patch employs an inner support layer.

FIG. 7 shows an embodiment employing a structural support layer 706 attached to a surface of a patch 702. The support layer 706 may be used to provide a more uniform force to the patch and the target site during deployment than if the patch did not have the reinforcing layer. The support layer 706 may be made from materials that are rigid, yet remain flexible enough to allow the patch to remain bonded to the target site even as the lumen moves, bends, expands, or contracts. These materials may include braided chord and various polymers.

Figure 8:
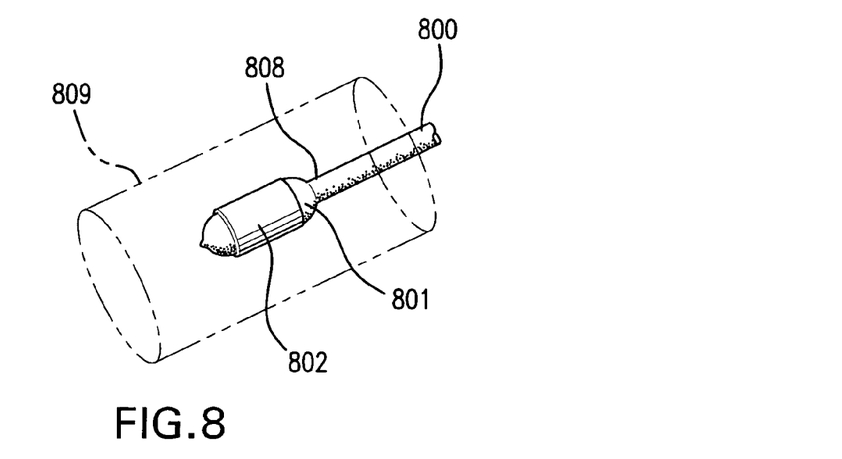
FIG. 8 is a perspective view of another embodiment of the present invention showing an intraluminal patch being advanced toward a target site.
Figure 9:
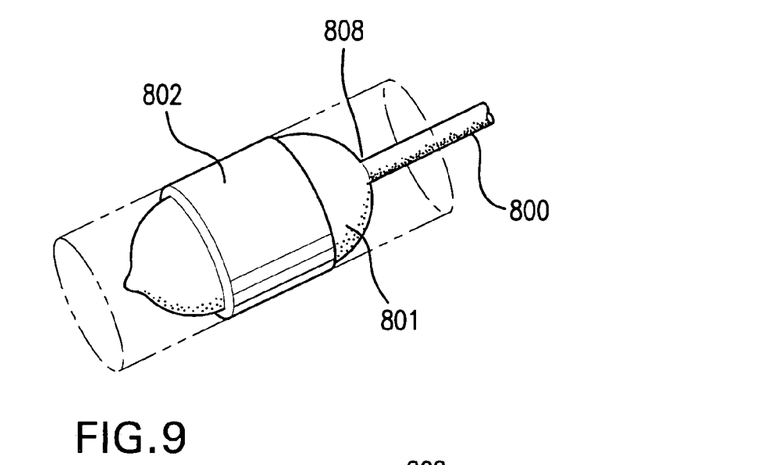
FIG. 9 is a perspective view of the embodiment of FIG. 8, after the device is expanded at the target site.
Figure 10:
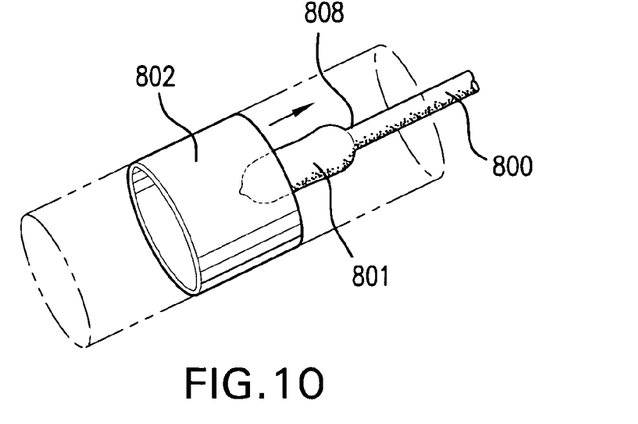
FIG. 10 is a perspective view of the embodiment of FIG. 8, as the device is being withdrawn from the target site.

FIGS. 8-10 shows steps that may be taken when deploying an intraluminal patch in accord with the present invention. In FIG. 8, an expandable therapeutic delivery device 808 is shown positioning an intraluminal patch 802 at a target site in a lumen 809. The delivery device 808 has reached the target site after being advanced through the lumens of the body. Once the intraluminal patch 802 is near the target site, the balloon 801 may be expanded, as shown in FIG. 9, allowing the adhesive region to contact and bond to the tissue surrounding the target site. After the intraluminal patch 802 is securely adhered to the target site, the expandable balloon 801 may be deflated, as shown in FIG. 10, and the drug delivery device 808 may be withdrawn, leaving the intraluminal patch in place.

Figure 11:
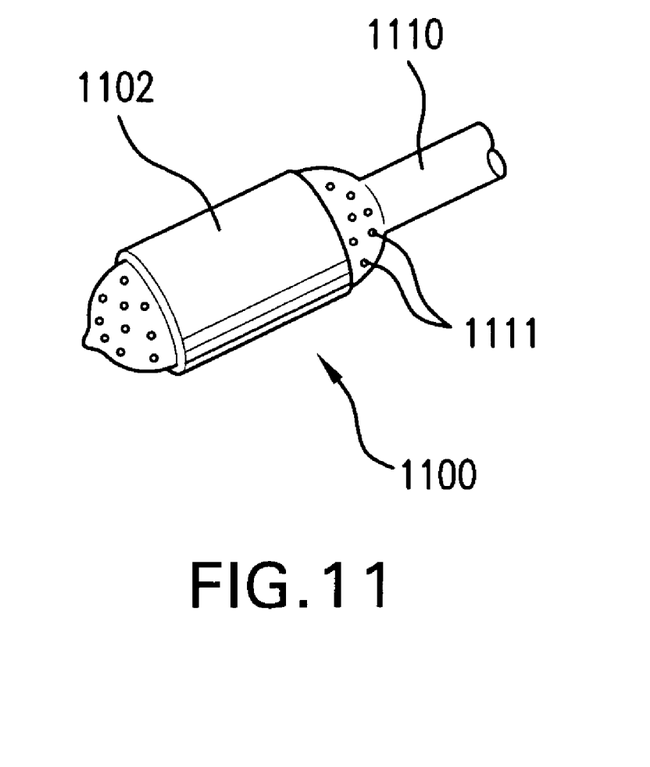
FIG. 11 is a perspective view of another embodiment of the present invention.

FIG. 11 is an alternative embodiment wherein the delivery device 1100 includes a balloon 1110 with perfusions 1111. The perfusions 1111 may be fluidly connected to catheter 1110 and may be used to actively deliver therapeutic or adhesive during a medical procedure in addition to the therapeutics and adhesives on the patch or in lieu of those materials.

Figure 12:
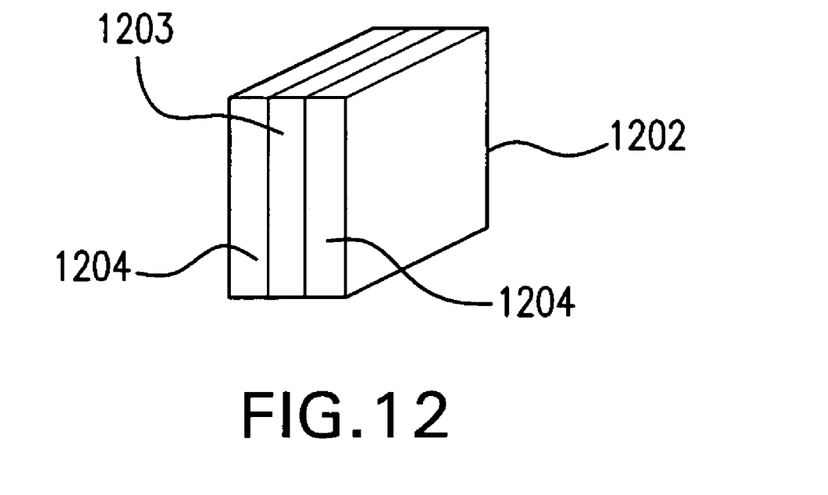
FIG. 12 is a perspective view of another embodiment of the present invention.

In the embodiment of FIG. 12 the patch 1202 has a drug impregnated polymer resin region 1203 and a protective region 1204 on both of its sides. The protective regions 1204 may also be impregnated with therapeutic. Alternatively, the protective regions 1204 may be only on one side of the polymer resin region. If more than one protective region 1204 is used, the composition of each protective region 1204 may have differing compositions. The polymer resin region 1203 may include a stoma adhesive. One or both protective regions 1204 may be peeled off prior to applying the patch 1202 to the target site. The patch 1202 may be applied directly to the target site using a means other than an expandable delivery device, e.g., by hand.

Figure 13:
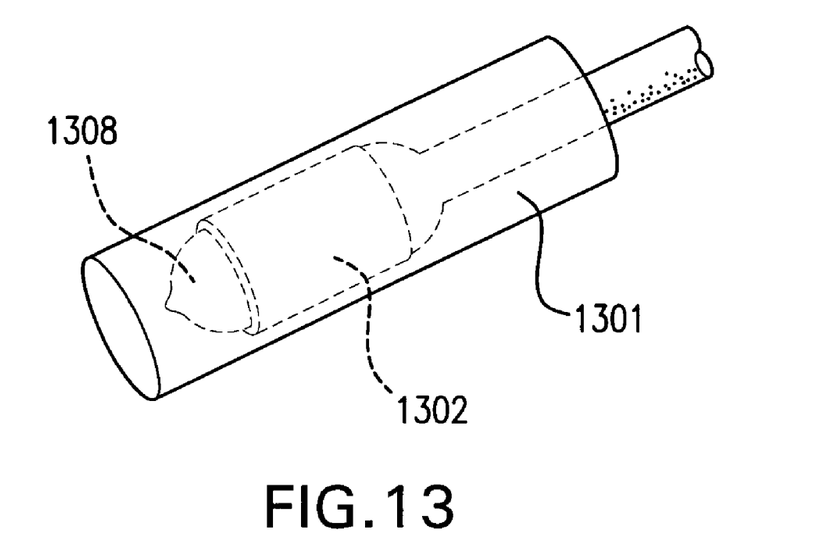
FIG. 13 is a perspective view of another embodiment of the present invention.
Figure 14:
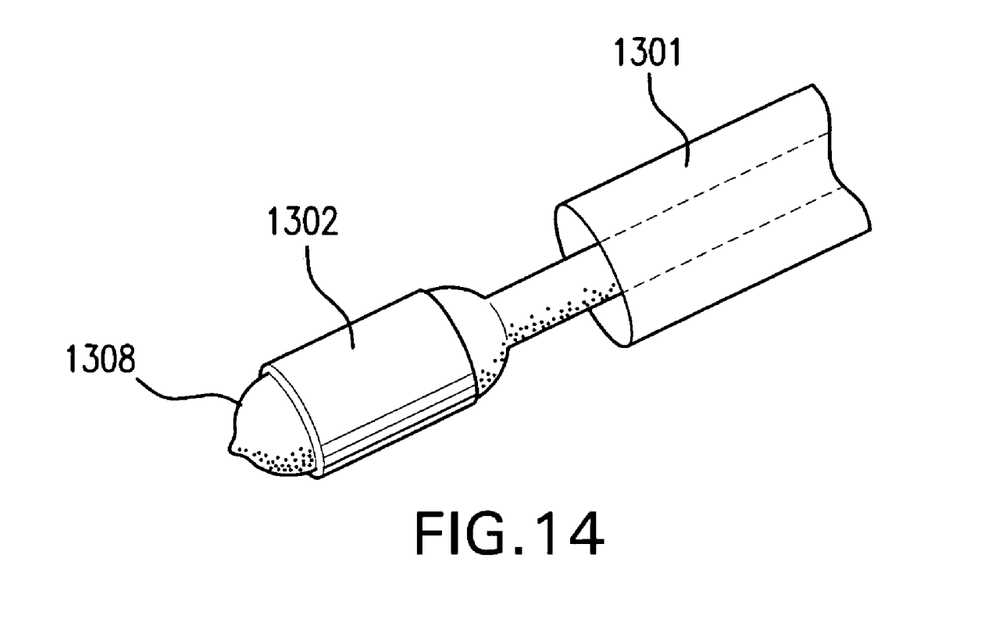
FIG. 14 is a perspective view of the embodiment of FIG. 13 showing the protective sheath being slid away from the intraluminal patch and the expandable balloon.

In the embodiment of FIGS. 13 and 14, the patch 1302 may be delivered using an expandable delivery device 1308, similar to the device in FIGS. 8-10, however the catheter has a coaxial protective sheath 1301, which is slidably disposed on the catheter. Prior to deployment, as shown in FIG. 13, the protective sheath may be slid distally until the sheath covers the exterior of the patch. Once the delivery device is near the target site, the protective sheath may be slid proximally, as shown in FIG. 14, to expose the patch to the environment at the target site.

The current invention can be utilized in a variety of medical procedures. For example, the intraluminal patch may be used as a patch during operations for bladder diverticulum, hernia repair, or during TURP procedures to cover and protect the area that had the procedure. The intraluminal patch may also be used during an aneurysm repair, or during gastrointestinal repair. The intraluminal patch may also be filled with barium or any type of radiopaque material for use during such operations as fluoroscopy.

Typical target sites include vascular, as well as non-vascular applications, such as neurological and gastrointestinal applications. The current invention also relates to anastomosis in the veins, arteries, intestinal tract or other injured areas. The current invention also relates to covering and sealing an injury in the esophagus.

The current invention may also be used during paving. Paving is a process where a polymer is positioned at a target site and is then molded into the shape of the target site by using heat. This heat can be provided by the balloon on the catheter.

The patch can be formed in the shape of a sheet, a tube or any other shape suitable to deploy at a specific target site inside the body. The layers of the patch may be formed from a polymer. The polymer may be dissolvable, absorbent, resilient, breathable or any combination of these properties.

The layers of the patch may also be made from a hydrogel polymer, including water soluble or water swellable thermoplastic polymers, as disclosed in U.S. Pat. No. 6,409,716 by Sahatjian, et al. The layers of the patch may also be formed from hydroxypropylcellulose or polyethylene oxide, as disclosed in U.S. Pat. No. 6,375,963 by Repka, et al., and in U.S. Pat. No. 6,162,456 by Dunbar, et al.

The layers that form the intraluminal patch may comprise a polymeric material/drug agent matrix formed, for example, by mixing a drug agent with a liquid polymer, in the absence of a solvent, to form a liquid polymer/drug agent mixture. Curing of the mixture typically occurs in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/drug agent mixture.

The polymers of the polymeric coatings may be biodegradable or non-biodegradable. Non-limiting examples of suitable non-biodegradable polymers include polystyrene; polyisobutylene copolymers and styrene-isobutylene-styrene block copolymers such as styrene-isobutylene-styrene tefl-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and poly-caprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

The polymer layers may also be formed from a low temperature resin that will soften at the body temperature and will mold to the shape of the surface at the target site. For example, a memory plastic produced by Mitsubishi Plastics in Japan may be used, in which a substrate layer comprising an adhesive combined with a drug would be used to bond to the target site. This memory plastic may be designed so that the plastic softens at a designated temperature. For example, the plastic may soften at 98° F. so that the patch softens in order to allow the patch to conform to the shape of the target site upon deployment inside a human body. The memory plastic may be designed to have varying degrees of softness according to the temperature. For example, as the temperature increases, the memory plastic becomes more pliable.

The regions of the patch may also be formed from a porous polymer platform for growing cells. The porous structure allows the patch to be used as a scaffold for cell replication. This embodiment is suitable for various gene therapy procedures, which holds the genes at the target site for sustained periods to allow the genes to proliferate to the target site. Once the patch is deployed, the patch dissolves leaving the new cells at the target site.

The patch may completely dissolve over time or may only partially dissolve, leaving some portion of the patch at the target site. In certain applications, the polymer does not dissolve, and can simply be removed when not needed.

The intraluminal patch may have a pressure sensitive adhesive region that holds the patch at the target site with an adhesive force related to the amount of pressure initially used to deploy the patch. The adhesive region may also be activated by a chemical means and by elevated temperatures. The adhesive region may also be a hydrocolloid adhesive, which is both an adhesive and an absorbent.

For target sites in high moisture environments, a multi-layered medical grade pressure sensitive adhesive may be used. For this situation, the adhesive region may have high moisture vapor transmission capabilities to allow for moisture evaporation from the wound area.

A stoma type adhesive, which is typically used to attach and strain relief catheters to patients, may be used in the adhesive layer. The stoma adhesive can be used in a fluid environment, and may also contain a therapeutic to prevent infection at the target site. Any of the adhesives discussed may also contain therapeutic. The adhesive layer may use any combination of these types listed, as well as other types known to one ordinarily skilled in the art.

In addition to, or as an alternative to, an adhesive region, the current invention may also provide for some other form of securement to the target site. For example, sutures may be used to attach the intraluminal patch to the target site, with or without the existence of an adhesive region.

The intraluminal patch, as discussed throughout, may contain a drug reservoir region. The release of therapeutic from the drug reservoir region may be triggered or controlled by the absorption of fluids from the target site, or the environment of the target site. For example, once the intraluminal patch has absorbed a certain amount of moisture, then the drugs may be released. Alternatively, the absorption of moisture into the intraluminal patch may act to displace the drugs, so that the drugs are released from the patch so long as moisture is being absorbed. Once a predetermined maximum amount of moisture has been absorbed by the patch, the patch may dissolve slowly or loose its adhesiveness and separate from the target site, while not damaging the target site or surrounding area.

The current invention may have multiple drug or therapeutic reservoir regions that dissolve slowly over time. The number of regions may be determined by the amount of time the drug is needed at the target site. The multiple drug reservoir regions may vary in thickness and composition.

Each drug or therapeutic reservoir region may contain only one drug or a combination of drugs. These regions may be separated from one another by a region of wax or other dissolvable polymer, so that as one drug reservoir region melts away, the next drug reservoir region is exposed.

The term "drug" and "therapeutic" as used herein includes one or more "therapeutic agents" or "drugs." The terms "therapeutic" and "drugs" are used interchangeably herein and include pharmaceutically active compounds, nucleic acids with and/or without carrier vectors such as lipids, compacting agents (such as histones), virus (such as adenovirus, adenoassociated virus, retrovirus, lentivirus and a-virus), polymers, hyaluronic acid, proteins, cells and the like, with or without targeting sequences. The therapeutic agent may be any pharmaceutically acceptable agent such as a non-genetic therapeutic agent, a biomolecule, a small molecule or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; bioflim synthesis inhibitors such as non-steroidal anti-inflammatory agents and chelating agents such as ethylenediaminetetraacetic acid, O,O'-bis (2-aminoethyl)ethyleneglycol -N,N,N',N'-tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; angiotensin converting enzyme (ACE) inhibitors; beta-blockers; bAR kinase (bARKct) inhibitors; phospholamban inhibitors; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include serca-2 protein, monocyte chemoattractant proteins ("MCP-1) and bone morphogenic proteins ("BMPs"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase; SERCA 2 gene; and combinations thereof. Non-limiting examples of angiogenic factors include acidic and basic fibroblast growth factors, vascular endothelial growth factor, epidermal growth factor, transforming growth factor and, platelet-derived endothelial growth factor, platelet-derived growth factor, tumor necrosis factor, hepatocyte growth factor, and insulin like growth factor. A non-limiting example of a cell cycle inhibitor is a cathepsin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin$^-$) cells including Lin$^-$CD34$^-$, Lin$^-$CD34$^+$, Lin$^-$cKit$^+$, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts +5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

Any of the therapeutic agents may be combined to the extent such combination is biologically compatible.

Any of the above mentioned therapeutic agents may be incorporated into a polymeric coating on the medical device or applied onto a polymeric coating on the medical device.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the intraluminal patch by any known method in the art including dipping, spraying, rolling, brushing, electrostatic plating or spinning, vapor deposition, air spraying including atomized spray coating, and spray coating using an ultrasonic nozzle.

The coating is typically from about 1 to about 50 microns thick. Very thin polymer coatings, such as about 0.2-0.3 microns and much thicker coatings, such as more than 10 microns, are also possible. It is also within the scope of the present invention to apply multiple layers of polymer coatings onto the patch. Such multiple layers may contain the same or different therapeutic agents and/or the same or different polymers. Methods of choosing the type, thickness and other properties of the polymer and/or therapeutic agent to create different release kinetics are well known to one in the art.

The intraluminal patch may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

The intraluminal patch may be implanted or otherwise utilized in body lumina and organs such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, and the like.

The intraluminal patch may also contain a drug that is toxic to the local area or the rest of the body, in order to destroy unwanted cells.

The present invention is not limited to the above embodiments. Rather, various elements from the above embodiments may be interchanged and combined in other ways while remaining within the spirit and scope of the present invention.

What is claimed is:

1. A therapeutic delivery system comprising:
    an intraluminal patch comprising at least one adhesive region and at least one therapeutic reservoir region, the patch sized to fit within a lumen of a human being, the adhesive region on an exposed surface of the patch;
    an expandable delivery device having an expandable balloon, the intraluminal patch being disposed over the expandable balloon; and
    a sheath slidably disposed on the expandable delivery device, the sheath positioned to slide over the intraluminal patch.

2. The therapeutic delivery system of claim 1, wherein at least one region of the intraluminal patch is dissolvable in water.

3. The therapeutic delivery system of clam 1, wherein the intraluminal patch further comprises at least one protective region, the protective region covering the adhesive region.

4. The therapeutic delivery system of claim 3, wherein at least one region of the intraluminal patch dissolves at a pre-selected rate.

5. The therapeutic delivery system of claim 1, wherein the intraluminal patch further comprises at least one support region, the support region providing additional strength to the patch.

6. The therapeutic delivery system of claim 1, wherein at least one region of the intraluminal patch is formed from a porous polymer platform for growing cells.

7. The therapeutic delivery system of claim 1, wherein at least one region of the intraluminal patch is a memory plastic that has varying degrees of softness depending on its temperature.

8. The therapeutic delivery system of claim 1, wherein the intraluminal patch is folded when disposed on the balloon.

9. The therapeutic delivery system of claim 1 wherein the balloon defines a plurality of micro-orifices.

10. The therapeutic delivery system of claim 1 wherein the release of the drug from the drug region is affected by a release control agent.

11. The therapeutic delivery system of claim 1, where at least one of the regions of the patch is formed from a polymer.

12. The therapeutic delivery system of claim 1, where the adhesive region is formed from a pressure sensitive adhesive.

13. A method of delivering therapeutics comprising:
    placing an intraluminal patch over an expandable delivery device, the expandable delivery device having an expanded and contracted position, and wherein a sheath is slidably disposed on the expandable delivery device, the sheath positioned to slide over the intraluminal patch;
    advancing the delivery device to a target site;
    exposing the intraluminal patch by sliding the sheath proximally;
    expanding the delivery device so that the patch adheres to the target site;
    isolating the target site from surrounding area with said patch;
    contracting and withdrawing the delivery device, leaving the patch at the target site; and
    emitting a drug from the intraluminal patch to the target site over a sustained period of time.

14. The method of claim 13, further comprising:
    absorbing moisture from the target site area into the intraluminal patch.

15. A method of delivering therapeutic comprising:
    providing an intraluminal patch having multiple regions, wherein the intraluminal patch is covered by a sheath;
    delivering the intraluminal patch to a target site;
    bonding the intraluminal patch to the target site;
    absorbing moisture into the intraluminal patch; and
    releasing a drug from within the intraluminal patch to the target site as the moisture is absorbed by the intraluminal patch.

16. The method of claim 15, further comprising:
    dissolving at least one region of the intraluminal patch.

* * * * *

UNITED STATES PATENT AND TRADEMARK OFFICE
CERTIFICATE OF CORRECTION

PATENT NO. : 7,402,172 B2  Page 1 of 1
APPLICATION NO. : 10/962689
DATED : July 22, 2008
INVENTOR(S) : Chin et al.

It is certified that error appears in the above-identified patent and that said Letters Patent is hereby corrected as shown below:

Column 2, lines 5-6, "employing" should be changed to --employs--;
Column 2, line 62, "able urge" should be changed to --able to urge--;
Column 4, line 11, "shows" should be changed to --show--;
Column 4, line 27, "balloon 1110" should be changed to --balloon--;
Column 4, line 31, "patch" should be changed to --patch 1102--;
Column 5, lines 45-46, "tefl-block copolymers" should be changed to --tert-block copolymers--;
Column 5, line 56, "BAYHDROL" should be changed to --BAYHYDROL--;
Column 5, line 63, "poly(D,L,-lactide)" should be changed to --(poly(D,L-lactide)--;
Column 5, line 64, "(DL-lactide-co-glycolide)" should be changed to --(D,L-lactide-co-glycolide)--;
Column 7, line 8, "loose" should be changed to --lose--;
Column 7, line 26, "virus" should be changed to --viruses--;
Column 7, line 27, "a-virus" should be changed to --α-virus--;
Column 8, line 24, "("MCP-1")" should be changed to --("MCP-1")--;
Column 8, line 27, "BMPS" should be changed to --BMPs--;
Column 8, line 34, "DNA's" should be changed to --DNAs--;
Column 8, line 40, "transforming growth factor and" should be changed to --transforming growth factor α and β--;
Column 8, line 42, "tumor necrosis factor" should be changed to --tumor necrosis factor α--;
Column 8, line 50, "have" should be changed to --having--; and
Column 8, line 62, "go cells" should be changed to --$G_o$ cells--.

Signed and Sealed this

Twenty-fifth Day of August, 2009

David J. Kappos
*Director of the United States Patent and Trademark Office*